(12) United States Patent
Yoshida et al.

(10) Patent No.: US 8,454,625 B2
(45) Date of Patent: Jun. 4, 2013

(54) INSERTION DEVICE FOR INTRAOCULAR LENS AND INTRAOCULAR LENS PRELOADED INSERTION DEVICE

(75) Inventors: Katsumi Yoshida, Yoshikawa (JP); Kenichi Kobayashi, Tokyo (JP)

(73) Assignee: STAAR Japan Inc., Urayasu-Shi, Chiba (JP)

( * ) Notice: Subject to any disclaimer, the term of this patent is extended or adjusted under 35 U.S.C. 154(b) by 57 days.

(21) Appl. No.: 12/629,667

(22) Filed: Dec. 2, 2009

(65) Prior Publication Data

US 2010/0076450 A1    Mar. 25, 2010

Related U.S. Application Data

(63) Continuation of application No. PCT/JP2008/060360, filed on Jun. 5, 2008.

(30) Foreign Application Priority Data

Jun. 5, 2007  (JP) ................................. 2007-149800

(51) Int. Cl.
*A61F 9/00* (2006.01)
*A61F 2/16* (2006.01)

(52) U.S. Cl.
USPC ........................................ 606/107; 623/6.12

(58) Field of Classification Search
USPC ................... 606/107, 166; 623/6.12
See application file for complete search history.

(56) References Cited

U.S. PATENT DOCUMENTS

| 4,325,375 | A |   | 4/1982  | Nevyas |         |
|-----------|---|---|---------|--------|---------|
| 4,634,423 | A |   | 1/1987  | Bailey, Jr. |   |
| 4,699,140 | A | * | 10/1987 | Holmes et al. | 606/107 |
| 5,190,552 | A | * | 3/1993  | Kelman | 606/107 |
| 5,944,725 | A | * | 8/1999  | Cicenas et al. | 606/107 |
| 6,355,046 | B2| * | 3/2002  | Kikuchi et al. | 606/107 |
| 6,770,093 | B2|   | 8/2004  | Worst et al. |     |
| 6,858,033 | B2|   | 2/2005  | Kobayashi |       |
| 7,156,854 | B2|   | 1/2007  | Brown et al. |    |

FOREIGN PATENT DOCUMENTS

| JP | 2003-325572 A | 11/2003 |
| JP | 2005-515027 A | 5/2005  |

OTHER PUBLICATIONS

International Bureau of WIPO, "PCT International Preliminary Report on Patentability", dated Jan. 21, 2010, pp. 1-4.

(Continued)

*Primary Examiner* — Kathleen Holwerda
*Assistant Examiner* — Sarah W Aleman
(74) *Attorney, Agent, or Firm* — John K. Fitzgerald; Fulwider Patton LLP

(57) ABSTRACT

The insertion device (2) for inserting an intraocular lens (1) into an eye includes a main body (12) including a lens housing portion (12b) in which the lens is housed and a nozzle portion (12c) for ejecting the lens into the eye, a pushing shaft (16) moving the lens from the lens housing portion and pushes out the lens into the eye through a front end opening (12j) of the nozzle portion, a first flow path configured to cause liquid to flow between the front end opening of the nozzle portion and an opening other than the front end opening, and a second flow path configured to cause liquid to flow between a portion (30a) protruding from the front end opening of the nozzle portion and an outside of the insertion device.

3 Claims, 15 Drawing Sheets

OTHER PUBLICATIONS

State Intellectual Property Office of the People's Republic of China, "Notification of the Second Office Action," from counterpart Chinese Patent Application No. 200880018846.0, dated Dec. 23, 2011.

International Bureau of WIPO, "International Search Report," Aug. 19, 2008, p. 1-3.
Prior Art Information List for PCT/JP2008/060360, p. 1.

* cited by examiner

INSERTION DEVICE FOR INTRAOCULAR LENS AND INTRAOCULAR LENS PRELOADED INSERTION DEVICE

CROSS-REFERENCES TO RELATED APPLICATIONS

This application is a continuation based on International Patent Application No. PCT/JP2008/060360, with an international filing date of Jun. 5, 2008, which claims priority from Japanese Application No. 2007-149800, filed Jun. 5, 2007, the contents of which are all hereby incorporated by reference herein in their entireties.

TECHNICAL FIELD

The present invention relates to an insertion device for inserting an intraocular lens into an eye, the intraocular lens being inserted thereinto instead of a crystalline lens after the crystalline lens is extracted because of cataract or in order to cure abnormal refraction.

BACKGROUND

In current cataract surgeries, first, a small incision is formed on an eyeball, and then a central portion of an anterior capsule of the eyeball is ablated by a surgical instrument inserted from the incision. Next, a phacoemulsification hand-tip connected to an ultrasonic phacoemulsification apparatus is inserted into the eyeball through the incision, to crush (emulsify) a clouded crystalline lens to remove (aspirate) it. Further, cortex which has not been removed by the ultrasonic phacoemulsification apparatus is removed using an I/A tip (irrigation aspiration tip) which is connected to the ultrasonic phacoemulsification apparatus and inserted through the incision into the eyeball. In this way, an artificial intraocular lens (hereinafter simply referred to as "lens") is placed at a position of the removed clouded crystalline lens and cortex. When the lens is inserted into the eyeball from the incision, the lens is deformed to be small by folding it or the like by utilizing flexibility of the lens.

In an actual surgery, an insertion device is frequently used which deforms the lens set in a main body of the device into a small shape while moving the lens in the main body by a pushing shaft, and pushes out the lens into the eyeball from a front end opening of an insertion cylinder (nozzle) inserted into the incision. Such an insertion device is used not only for the cataract surgery but also for a lens inserting surgery for an eyesight correction medical treatment.

When the lens is inserted into the eyeball by using the insertion device, a viscoelastic material such as sodium hyaluronate is introduced into the main body of the insertion device as a lubricant such that the lens is smoothly moved and deformed in the insertion device (see Japanese Patent Laid-Open No. 2004-351196). Moreover, the viscoelastic material introduced into the eyeball through the insertion cylinder has a function of spreading a space in an anterior chamber of the eyeball into which the lens will be inserted. In addition, it has been recently required to use inexpensive physiologic saline in place of the viscoelastic material.

Meanwhile, when the ultrasonic phacoemulsification apparatus is used for removing the crystalline lens from the eyeball, insertion and withdrawal of the ultrasonic phacoemulsification apparatus (that is, of the phacoemulsification hand-tip and the I/A tip) with respect to the incision formed on the eyeball are performed at least twice. Moreover, when the lens is inserted into the eyeball by using the lens insertion device, insertion and withdrawal of the ultrasonic phacoemulsification apparatus and the insertion device with respect to the incision are performed at least three times in total. Such repetition of insertion and withdrawal with respect to the incision increases a burden on the eyeball.

SUMMARY OF THE INVENTION

The present invention provides an insertion device for an intraocular lens capable of reducing a burden on an eyeball on which an incision is formed.

The present invention provides as one aspect thereof an insertion device for inserting an intraocular lens into an eye. The insertion device includes a main body configured to include a lens housing portion in which the intraocular lens is housed and a nozzle portion for ejecting the lens into the eye, a pushing shaft configured to move the lens from the lens housing portion and pushes out the lens into the eye through a front end opening of the nozzle portion, a first flow path configured to cause liquid to flow between the front end opening of the nozzle portion and an opening other than the front end opening, and a second flow path configured to cause liquid to flow between a portion protruding from the front end opening of the nozzle portion and an outside of the insertion device.

The present invention provides as another aspect thereof an intraocular lens preloaded insertion device including the insertion device, and an intraocular lens held in the lens housing portion of the insertion device.

The present invention provides as still another aspect thereof a method for manufacturing an intraocular lens preloaded insertion device. The manufacturing method includes a step of preparing the above-described insertion device, and a step of causing the lens housing portion of the insertion device to hold the intraocular lens.

Other aspects of the present invention will become apparent from the following description and the attached drawings.

DETAILED DESCRIPTION OF THE PREFERRED EMBODIMENTS

Exemplary embodiments of the present invention will hereinafter be described with reference to the accompanying drawings.

Figure 1A:
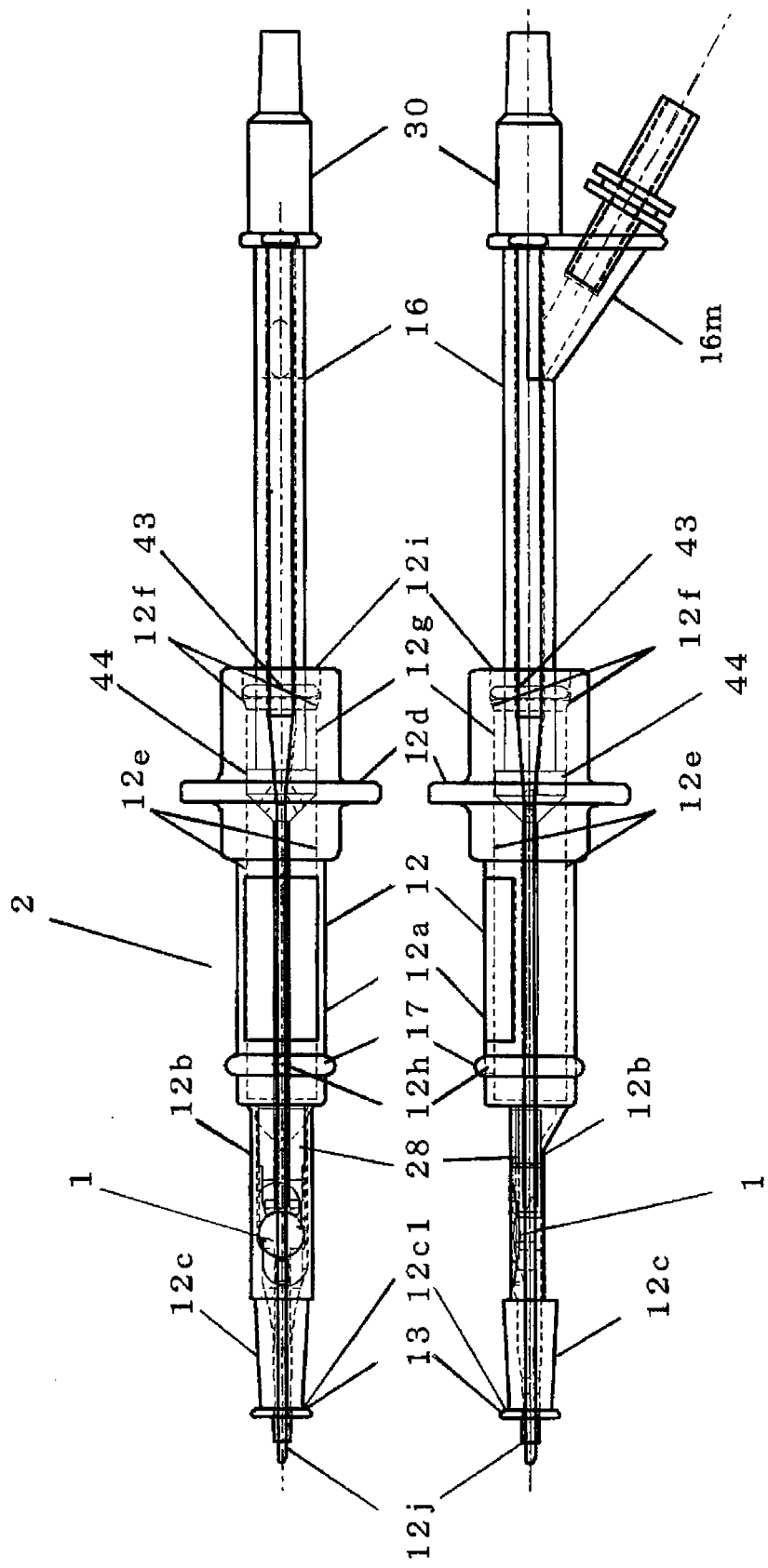
FIG. 1A is a top view and a side view of an insertion device for an intraocular lens, which is an embodiment of the present invention.
Figure 1B:
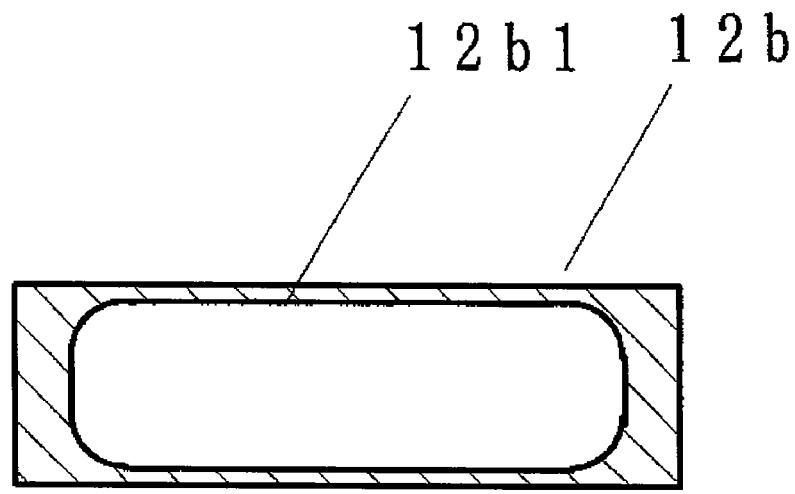
FIG. 1B is a sectional view of a lens housing portion in a main body of the insertion device of the embodiment.
Figure 2A:
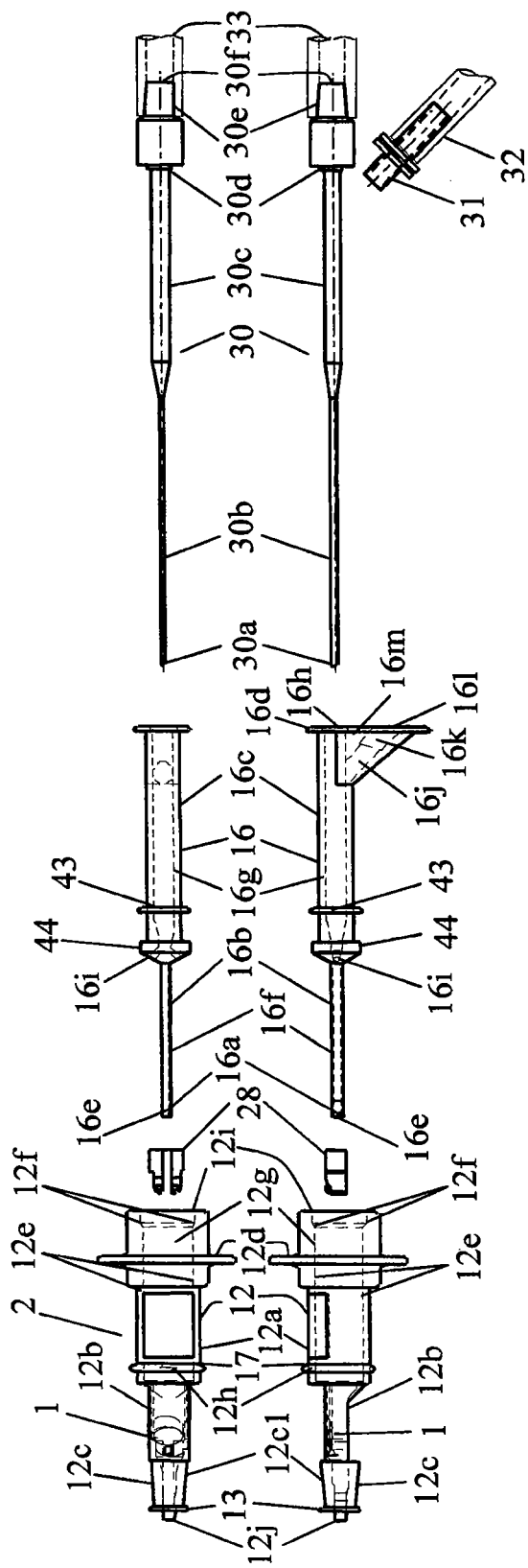
FIG. 2A is a top view and a side view before assembly of the main body and a pushing shaft of the insertion device of the embodiment.

FIG. 1A shows an insertion device for an intraocular lens (hereinafter simply referred to as "lens") which is an embodiment of the present invention. An upper part in FIG. 1A shows a top view, and a lower part shows a side view. FIGS. 1A and 1B show a compressed shape of the insertion device in an axial direction described below. FIG. 2A shows a state before a pushing shaft is assembled to a main body, which will be described below, of the insertion device. An upper part in FIG. 2A shows a top view and a lower part shows a side view.

In the description below, a nozzle side is referred to as "front (end) side", and a side opposite to the nozzle side is referred to as "rear (end) side". A direction extending toward the front and rear sides is referred to as "axial direction" of the insertion device, and a direction perpendicular to the axial direction is referred to as "up-and-down direction", "right-and-left direction" or "radial direction". Further, an axis extending parallel to the axial direction and passing through an inner space of the main body or a center of the lens is referred to as "central axis", and a direction around the central axis is referred to as "circumferential direction".

The insertion device 2 is basically constituted by a main body 12 with a nozzle (hereinafter simply referred to as "main body"), a lens holding member 28, a pushing shaft 16 and an aspiration shaft (aspiration tube) 30.

The main body 12 includes an outer cylindrical portion 12a as a hand-held portion having an outer diameter suitable for holding the insertion device 2 by hand, a lens housing portion 12b provided closer to a front end of the main body 12 than the outer cylindrical portion 12a and housing a lens holding member 28, and a nozzle portion 12c as an insertion cylindrical portion provided closer to the front end than the lens housing portion 12b. In a rear part of the outer cylindrical portion 12a, a flange portion 12d is formed as a portion supported by hand when pushing the pushing shaft 16. The main body 12 is an integrally formed member. The main body 12 has a hollow shape, and the lens holding member 28 and the pushing shaft 16 are inserted into the main body 12 through a rear end opening 12i thereof.

The outer cylindrical portion 12a includes, from the front end thereof to a position between the flange portion 12d and the outer cylindrical portion 12a, a first inner circumferential surface 12e having a cylindrical shape. At a part closer to the rear end than the first inner circumferential surface 12e, a second inner circumferential surface 12g having a cylindrical shape and a slightly smaller inner diameter than that of the first inner circumferential surface 12e is formed. Further, at a part closer to the rear end than the second inner circumferential surface 12g, a conical surface 12f is formed which has an increasing inner diameter toward the rear end. At a part closer to the rear end than the conical surface 12f, a third inner circumferential surface having a cylindrical shape and a larger inner diameter than that of the first inner circumferential surface 12e is formed up to the rear end opening 12i.

The nozzle portion 12c has decreasing inner and outer diameters toward the front end, and its part having a predetermined length from a front end opening 12j of the nozzle portion 12c is formed to be a thinnest part thereof which is an inserting part to be inserted into an eye (eyeball) through an incision formed on the eyeball. On an outer circumference of a rear end of the inserting part, a cover ring (O-ring) 13 made of an elastic member such as rubber is mounted. On a rear side of the cover ring 13 in the nozzle portion 12c, a step 12c1 is formed having a larger outer diameter than that of the inserting part for preventing rearward movement of the cover ring 13.

The lens housing portion 12b basically has a hollow flat plate shape having a vertical dimension smaller than a lateral dimension when viewed from the axial direction. A rear part of a lower surface of the lens housing portion 12b near a boundary between the lens housing portion 12b and the outer cylindrical portion 12a has a semi-conical shape having an increasing diameter toward the rear for reinforcement. Since the lens holding member 28 is inserted into the main body 12 through the rear end opening 12*i*, a continuous tapered connection part between an inner surface of the outer cylindrical portion 12*a* and an inner surface of the lens housing portion 12*b* provides an insertion guiding shape, thereby facilitating insertion of the lens holding member 28 into the main body 12.

The lens housing portion 12*b* can receive the insertion of the lens holding member 28 from the rear end thereof, and has an inner surface shape capable of stably holding the inserted lens holding member 28.

Figure 1C:
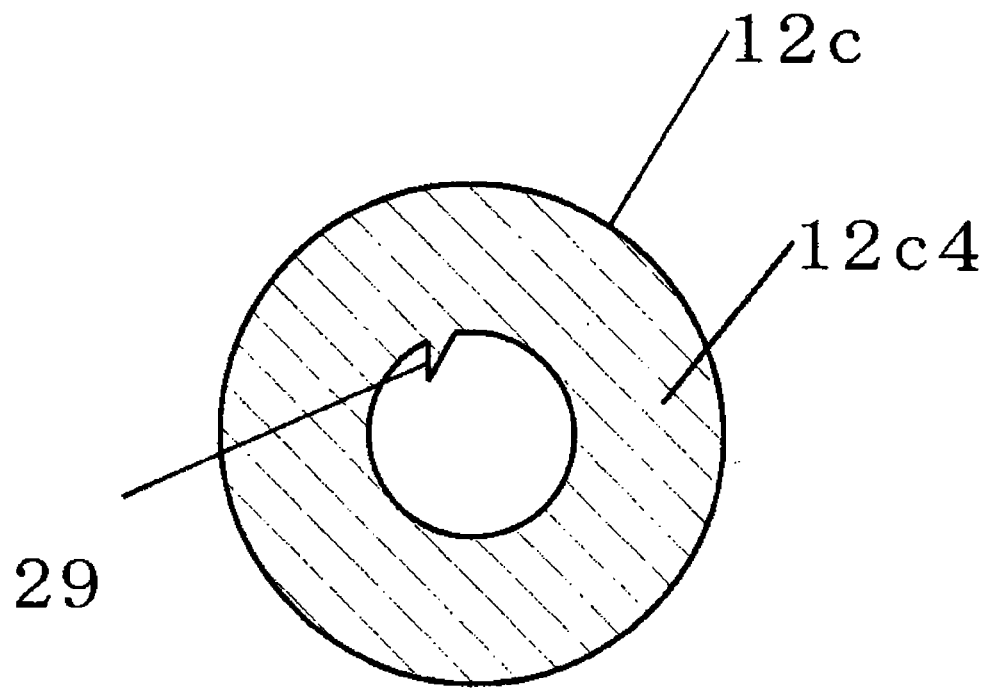
FIG. 1C is a sectional view of a nozzle portion in the main body of the insertion device of the embodiment.

FIGS. 1B and 1C respectively show sections orthogonal to the axial direction of the lens housing portion 12*b* and the nozzle portion 12*c*. Circumferential walls 12*b*1 and 12*c*4 are formed from the lens housing portion 12*b* to the nozzle portion 12*c* so as to be an integral wall without an opening and a gap. In other words, four side (upper, lower, right and left) walls surrounding a space thereinside are circumferentially connected, and integrally formed without an opening such as a hole and a dividable or openable/closable portion where a gap is formed in their parting line. Reference numeral 29 in FIG. 1C denotes a rail for guiding the lens 1 passing through an inside of the nozzle portion 12*c*.

This embodiment describes the case where the main body 12 is an integrally formed member such that at least the circumferential walls 12*b*1 and 12*c*4 formed from the lens housing portion 12*b* to the nozzle portion 12*c* have no opening or gap. However, an alternative embodiment of the present invention is not limited to this case. For example, the main body 12 may be constituted by joining by thermal welding or bonding two divided upper and lower members from their front end to their rear end to be integrated such that the main body 12 after its completion (before insertion of the lens holding member 28 into the main body 12) is an integral member without an opening and a gap at least in the circumferential walls from the lens housing portion 12*b* to the nozzle portion 12*c*.

Further, the main body 12 may be constituted by joining by thermal welding or bonding the lens housing portion 12*b*, nozzle portion 12*c* and outer cylindrical portion 12*a* produced separately from each other to be integrated such that the main body 12 after its completion (before insertion of the lens holding member 28 into the main body 12) is an integral member without an opening and a gap at least in the circumferential walls from the lens housing portion 12*b* to the nozzle portion 12*c*.

As shown by a dotted line in the top view in FIG. 1A, a small hole 12*h* is formed in a circumferential wall near the front end of the outer cylindrical portion 12*a*. This hole 12*h* is naturally formed for placing a supporting member that supports a die for forming the inner surface of the main body 12 when the main body 12 is produced, that is, the main body 12 is integrally formed of resin.

In this embodiment, in order to cover the hole 12*h*, an O-ring 17 made of an elastic member such as rubber is mounted on an outer circumference of the outer cylindrical portion 12*a*. The O-ring 17 enables provision of the main body 12 having no opening other than the rear end opening 12*i* in the outer cylindrical portion 12*a* and the front end opening 12*j* in the nozzle portion 12*c*.

A mounting surface for the O-ring 17 on an outer circumferential surface of the outer cylindrical portion 12*a* has a diameter smaller than those of surfaces thereon adjacent to the mounting surface on front and rear end sides. This prevents movement of the O-ring 17 on the outer cylindrical portion 12*a* in the axial direction. The O-ring 17 is provided at a position often touched by hand of an operator holding the insertion device 2. Thus, the O-ring 17 has a function of covering the hole 12*h* as well as a function of preventing the hand holding the insertion device 2 from slipping. However, if not covering the hole 12*h* does not directly influence flow of liquid described below, covering the hole 12*h* is not necessarily required and there is no problem in view of functions of the insertion device 2.

Figure 3:
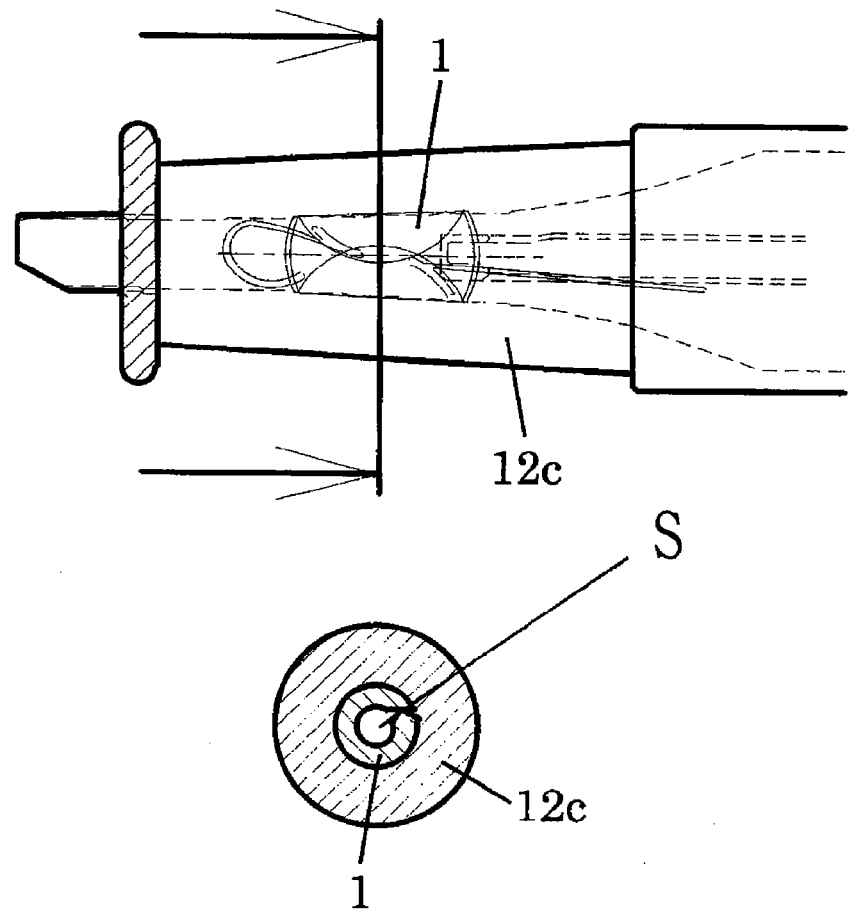
FIG. 3 is a view showing a state in which there is a space in a nozzle inside which a lens is folded in the embodiment.
Figure 4:
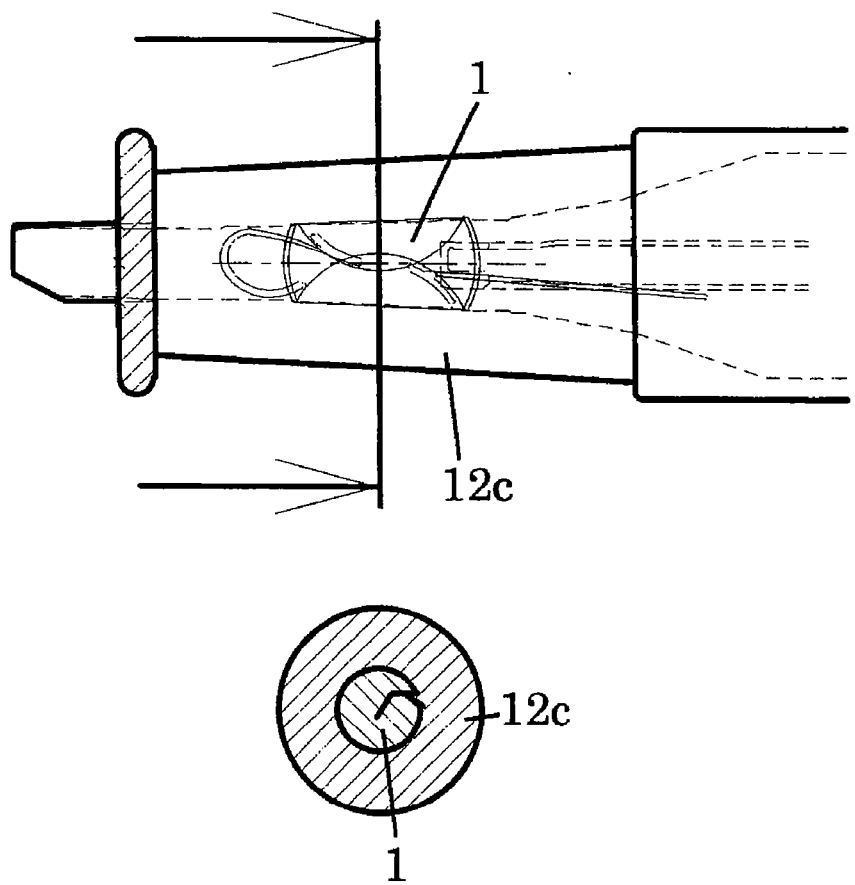
FIG. 4 is a view showing a state in which there is no space in the nozzle inside which the lens is folded in the embodiment.

Covering the hole 12*h* with the O-ring 17 is effective in a case where there is a space S in the nozzle portion 12*c* as shown in FIG. 3 when the lens 1 is folded in the nozzle portion 12*c*. However, because a thickness of the lens 1 varies depending on power and material thereof, in cases where a space in the nozzle portion 12*c* is reduced or removed when the lens 1 is folded thereinside as shown in FIG. 4, it is recommended that the hole 12*h* be opened as a liquid outlet.

The pushing shaft 16 includes, as shown in detail in FIG. 2A, a bifurcated portion 16*a* formed at its front end for gripping the lens 1, a thin shaft portion 16*b* having a thin outer diameter in order to pass through the inside of the nozzle portion 12*c*, a thick shaft portion 16*c* passing through the inside of the first inner circumferential surface 12*e* of the main body 12, and a flange portion 16*d* for pushing the pushing shaft 16 by hand into the main body 12.

Further, inside the thick shaft portion 16*c* a thick shaft hole 16*g* which opens (16*h*) at the flange portion 16*d* is formed, and in the thin shaft portion 16*b* a thin shaft hole 16*f* connected to the thick shaft hole 16*g* is formed. Further, the thin shaft hole 16*f* opens (16*e*) at the bifurcated portion 16*a*. Moreover, an intermediate hole 16*i* connected to outside of the pushing shaft 16 from the thick shaft hole 16*g* is formed between the thin shaft portion 16*b* and the thick shaft portion 16*c*.

Moreover, on an outer circumferential surface of the thick shaft portion 16*c*, a perfusion tube connecting portion 16*m* is formed so as to project therefrom. Inside the perfusion tube connecting portion 16*m*, a perfusion tube connecting hole 16*j* which opens (16*l*) at its rear end is formed. The perfusion tube connecting hole 16*j* is connected to the thick shaft hole 16*g*. At a rear end side part of the perfusion tube connecting hole 16*j*, a conical hole portion 16*k* which has an increasing inner diameter toward the rear end is formed.

The thick shaft portion 16*c* is formed such that an inner diameter of a rear end side part of the thick shaft hole 16*g* (part between a thick shaft hole 16*g* side opening of the perfusion tube connecting hole 16*j* and the rear end opening 16*h* of the thick shaft hole 16*g*) is slightly smaller than that of a front end side part thereof. Then, into the part having the slightly smaller inner diameter, a thick shaft portion 30*c* of an aspiration shaft 30 which will be described later is pressed. Thus, the rear end side part of the thick shaft portion 16*c*, inside which the thick shaft hole 16*g* is formed, serves as an aspiration shaft connecting portion (aspiration tube connecting portion) capable of connection of the aspiration shaft 30, which enables connection of the aspiration shaft 30 to the pushing shaft 16 (i.e., to the insertion device 2).

At a front end of the thick shaft portion 16*c* of the pushing shaft 16, a seal cap 44 for generating sliding resistance against the first inner circumferential surface 12*e* of the main body 12 is mounted. The seal cap 44 enables provision of appropriate operability of the pushing shaft 16 and prevention of liquid leakage from a sliding part between the main body 12 and the thick shaft portion 16*c*. The seal cap 44 includes a hole which is connected to the above-described intermediate hole 16*i* and opens at an outer surface of the seal cap 44.

Further, on the thick shaft portion 16*c*, a backlash preventing O-ring 43 is attached. The backlash preventing O-ring 43 is brought into press contact with the third inner circumferential surface of the main body 12 to restrict movement of the pushing shaft 16 except for movement thereof in the axial direction when the thick shaft portion 16c is inserted into the main body 12 to be assembled thereto through the rear end opening 12i of the main body 12. The backlash preventing O-ring 43 is slidable on the thick shaft portion 16c in the axial direction.

The aspiration shaft 30 has, as shown in detail in FIG. 2A, a thin shaft portion 30b having a front end portion 30a which is inserted into the eyeball for removing cortex in a cataract surgery, and the above-described thick shaft portion 30c formed in a part closer to the rear end than the thin shaft portion 30b. At a rear end side part of the thick shaft portion 30c, a conical portion 30e which is pressed into one end of an aspiration tube 33 to connect the aspiration tube 33 to the aspiration shaft 30 is formed. Further, on an outer circumference of the thick shaft portion 30c, an O-ring 30d for preventing leakage of perfusate with which the inside of the main body 12 is filled is attached. The perfusate will be described later. Another end of the aspiration tube 33 is connected to an ultrasonic phacoemulsification apparatus (not shown).

Figure 2B:
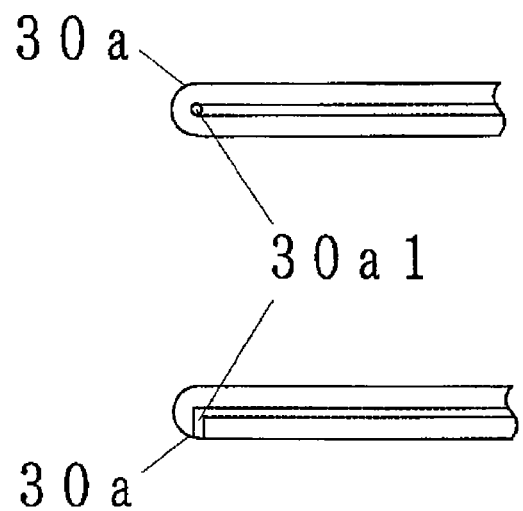
FIG. 2B is an enlarged view of a front end portion of an aspiration shaft in the embodiment.

At the front end portion 30a of the aspiration shaft 30, as shown in FIG. 2B, a hole 30a1 for aspirating cortex in the eyeball is formed. The hole 30a1 is connected to a rear end opening 30f formed at a rear end of the thick shaft portion 30c through the thin shaft hole formed inside the thin shaft portion 30b and the thick shaft hole formed inside the thick shaft portion 30c.

The aspiration shaft 30 thus formed can be inserted into the thick shaft hole 16g through the rear end opening 16h of the pushing shaft 16. The thin shaft portion 30b of the aspiration shaft 30 is capable of passing through the thin shaft hole 16f of the pushing shaft 16 to project to outside of the pushing shaft 16 through the opening 16e formed in the bifurcated portion 16a.

Figure 5:
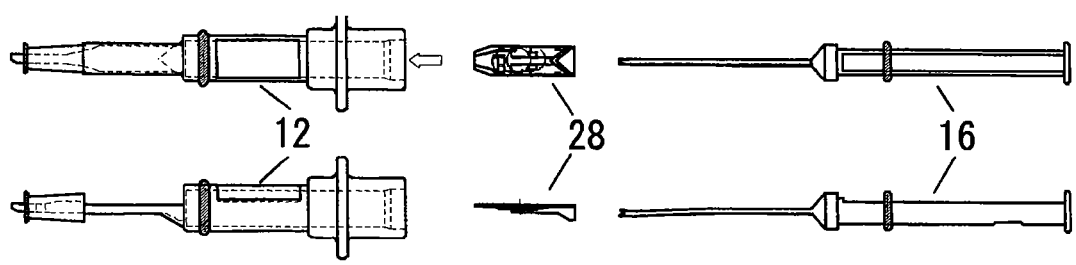
FIG. 5 is a top view and a sectional view showing a state before assembly of a main body and a pushing shaft in a conventional insertion device.

FIG. 5 shows a state before assembly of a conventional insertion device. In this drawing, components having common functions to those of the embodiment are denoted by the same reference numerals as those of the embodiment.

The lens holding member 28, which basically has a configuration similar to that of a lens holding member of this embodiment described later, includes a first holding member 28A that supports the lens 1 from below, and a second holding member 28B that retains from above the lens 1 in combination with the first holding member 28A. An upper part in FIG. 6 shows the first holding member 28A viewed from the top, and a lower part in FIG. 6 shows the first holding member 28A and the second holding member 28B viewed from the side.

First, a configuration of the lens 1 held by the lens holding member 28 will be described. The lens 1 has a circular shape in top view, and includes an optical portion 1a having a function of a lens and support portions 1b extending from both sides (right and left sides) of the optical portion 1a. Each of the right and left support portions 1b is a wire-like portion that elastically supports the optical portion 1a in the eyeball after the lens 1 is inserted into the eyeball.

A ring-shaped marginal portion 1c having upper and lower surfaces parallel to each other is formed around (that is, at a periphery of) the optical portion 1a. The marginal portion 1c is hereinafter referred to as "lens marginal portion 1c".

Figure 6:
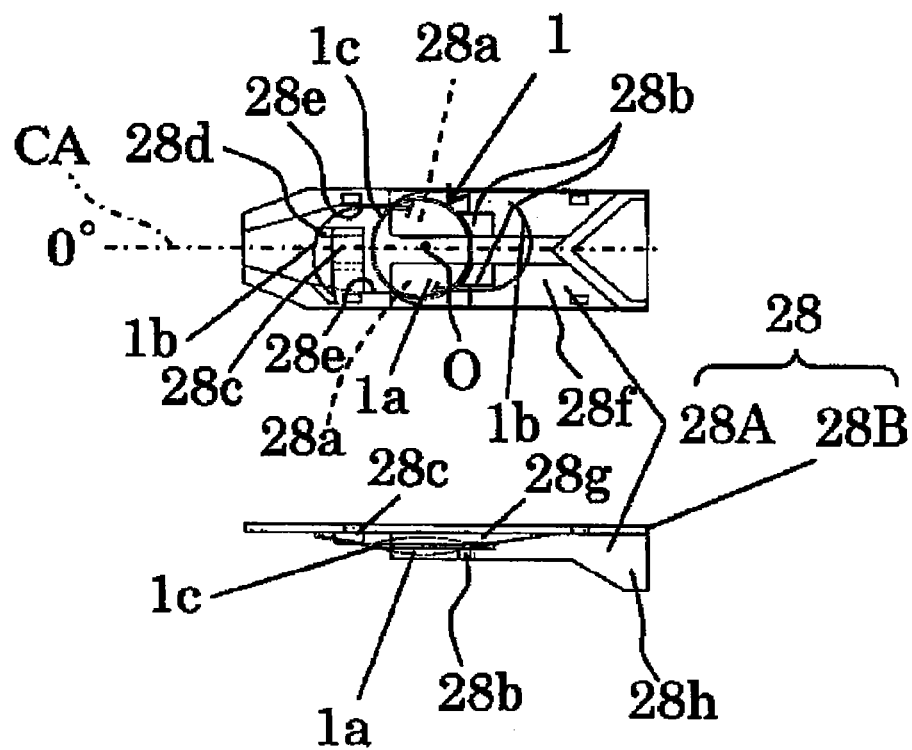
FIG. 6 is a top view and a side view showing an example of a lens holding member in the conventional insertion device.

As shown in FIG. 6, the first holding member 28A is formed symmetrically in the right-and-left direction with respect to a central axis CA passing through a center O of the optical portion 1a of the lens 1 except part thereof. Support surfaces 28a are formed at the right and left in a lower part of the first holding member 28A. Each of the support surfaces 28a is formed such that its inner part is lower than its outer part in the right-and-left direction (width direction).

In the top view in FIG. 6, a position in a direction toward the front end from the center O of the optical portion 1a in the lens marginal portion 1c (that is, a position on the central axis CA) is defined as a 0° position. The right and left support surfaces 28a contact first right and left arcuate regions in the lens marginal portion 1c to support them from below, the first right and left arcuate regions being regions between positions rearward away from the 0° position in both circumferential directions by a circumferential angle of 60° (hereinafter the positions of 60° are referred to as "60° positions", and other positions are hereinafter referred to as the same) and 90° positions rearward away from the 0° position by a circumferential angle of 90°.

At the right and left in a middle part of the first holding member 28A in the axial direction, support protrusions 28b are formed which support second right and left arcuate regions between 135° positions to 165° positions. The second right and left arcuate regions are closer to a rear end of the lens marginal portion 1c than the first right and left arcuate regions supported by the support surfaces 28a in the lens marginal portion 1c. A space through which the pushing shaft 16 (pushing shaft portion 16c) passes is formed between the support protrusions 28b. Since the space has only an angle width of 30°, it can be regarded that the support protrusions 28b support an arcuate region having an angle width of 90° around a 180° position in the lens marginal portion 1c. In other words, the first holding member 28A substantially supports the lens marginal portion 1c at three positions at 120° intervals including the right and left 60° positions and the 180° position.

Each of the support protrusions 28b has a horizontal surface on which the lens marginal portion 1c is placed and a vertical surface that contacts or comes close to an outer circumferential end surface of the lens marginal portion 1c on a rear side of the horizontal surface, supports the lens marginal portion 1c from below, and prevents rearward movement of the lens 1.

Further, at the right and left on a front end side of the first holding member 28A, right and left vertical surfaces 28e are formed that contact or come close to the 60° positions in the outer circumferential end surface of the lens marginal portion 1c. The right and left vertical surfaces 28e prevent movement of the optical portion 1a frontward before the lens 1 is pushed out by the pushing shaft 16.

At an upper part in the front end of the first holding member 28A, an arm 28c is formed extending from a right side to a left side (from a lower side to an upper side in the top view in FIG. 6). Further, at a tip of the arm 28c, a protrusion 28d that supports from below the front side support portion 1b is formed so as to extend toward the front end.

At a rear part of the first holding member 28A, an inclined surface 28f that supports from below the rear side support portion 1b is formed so as to become higher as a position approaches the rear end.

The second holding member 28B is placed above the first holding member 28A. The first and second holding members 28A and 28B are inserted into the lens housing portion 12b while holding the lens 1, and are held between a ceiling surface and a bottom surface of the lens housing portion 12b without mutual displacement.

The second holding member 28B is formed symmetrically in the right-and-left direction with respect to the central axis CA, though not shown. At right and left positions in a lower surface of the second holding member 28B, right and left retaining protrusions 28g are formed which contact or come close to third right and left arcuate regions from the 90° positions to 120° positions and the second right and left arcuate regions from the 135° positions to the 165° positions in the lens marginal portion 1c. A space through which the pushing shaft 16 (pushing shaft portion 16c) passes is formed between the right and left retaining protrusions 28g with the 180☐ position located therebetween.

Front end side parts of the right and left retaining protrusions 28g retain from above arcuate regions in the lens marginal portion 1c closer to the rear end thereof than the first right and left arcuate regions supported by the support surfaces 28a of the first holding member 28A. Rear end side parts of the right and left retaining protrusion 28g retain from above the second right and left arcuate regions of the lens marginal portion 1c supported from below by the support protrusions 28b of the first holding member 28A.

As shown in a side view in FIG. 6, the second holding member 28B is assembled to an upper side of the first holding member 28A, and thus the first right and left arcuate regions from the 60° positions to the 90° positions in the lens marginal portion 1c are supported from below by the support surfaces 28a of the first holding member 28A, and the third right and left arcuate regions from the 90° positions to the 120° positions in the lens marginal portion 1c are retained from above by the front end side parts of the right and left retaining protrusions 28g of the second holding member 28B. Further, the second right and left arcuate regions from the 135° positions to the 165° positions in the lens marginal portion 1c are vertically held by the horizontal surfaces of the support protrusions 28b of first holding member 28A and the rear end side parts of the right and left retaining protrusions 28g of the second holding member 28B therebetween. With such a holding structure, the lens 1 is supported in a state where the optical portion 1a of the lens 1 is held in a horizontal state and in a state where a stress by its own weight or an external force is not substantially applied on the optical portion 1a.

The state in which the "stress is not substantially applied on the optical portion" denotes a state where no stress is applied on the optical portion at all as well as a state where a minute stress is applied thereon such that a deformation influencing an optical function of the optical portion 1a after insertion of the lens 1 into the eye does not occur even if the lens 1 before insertion into the eye is held and stored for a long time. In other words, the state denotes a state where a stress or a deformation influencing the optical function of the optical portion 1a does not occur.

The right and left vertical surfaces 28e that contact the 60° positions in the outer circumferential end surface of the lens marginal portion 1c and vertical surfaces of the support protrusions 28b that contact right and left regions from the 135° positions to the 165° positions prevent frontward and rearward displacements of the lens 1. Further, a front end side 120° region of the lens marginal portion 1c is opened by providing the right and left vertical surfaces 28e in the 60° positions. This allows the lens 1 to be smoothly moved frontward from the lens holding member 28 when the lens 1 is pushed out by the pushing shaft 16.

At parts of the right and left retaining protrusions 28g of the second holding member 28B closer to the rear end than the parts retaining the lens marginal portion 1c, inclined portions are formed which extend in parallel with the inclined surface 28f of the first holding member 28A and sandwich the rear side support portion 1b together with the inclined surface 28f. Further, the right and left vertical surfaces 28e of the first holding member 28A are formed so as to extend in the front end direction along an outer edge of the front side support portion 1b. The contact of the right and left vertical surfaces 28e with the front side support portion 1b and the sandwiching of the rear side support portion 1b between the inclined surface 28f and the inclined portions of the retaining protrusions 28g prevent rotation of the lens 1.

The above-described configuration of the lens holding member 28 is an example. The method for holding the lens 1 in the lens housing portion 12b (configuration of a member holding the lens 1) is not limited thereto.

Figure 7:
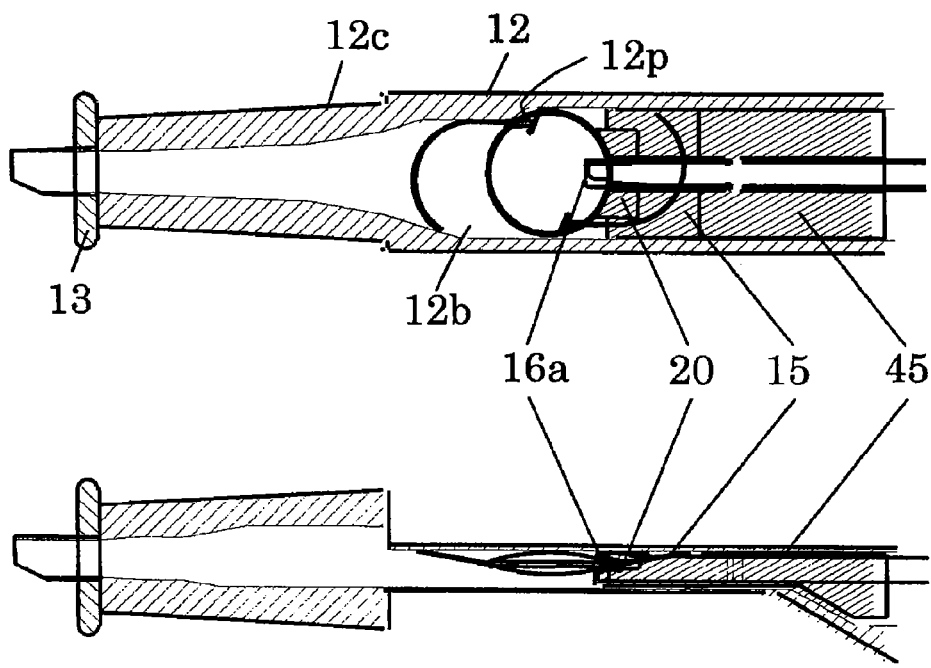
FIG. 7 is a top sectional view and a side sectional view of a lens holding member (an interlocking member) in the insertion device of the embodiment.
Figure 9A:
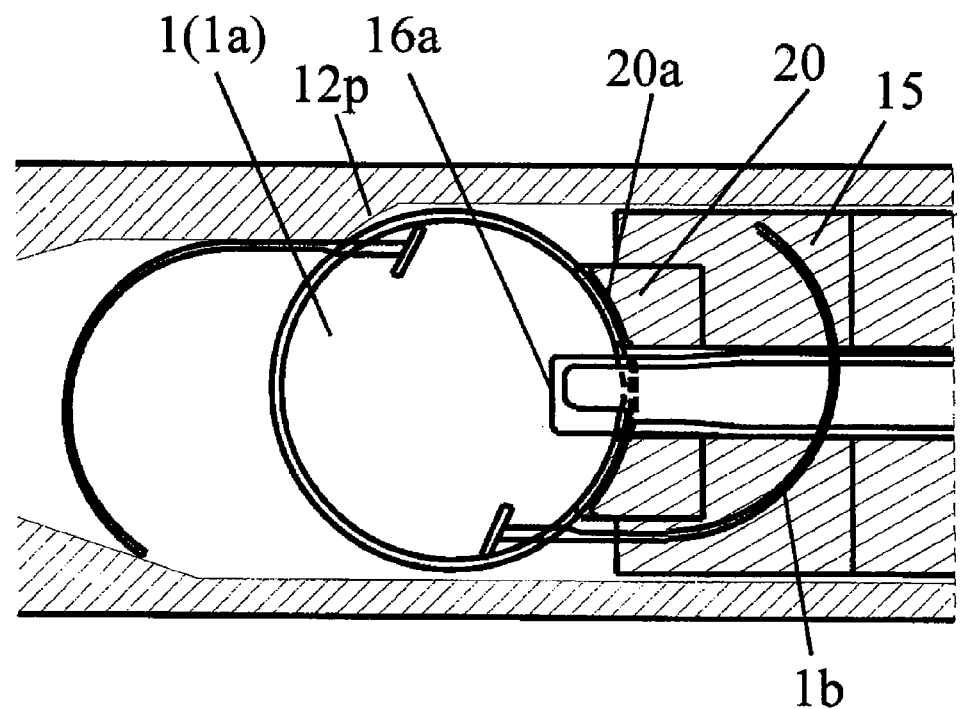
FIG. 9A is a top view showing a case where a vertical surface for preventing displacement of the lens and an outline of the lens have similar shapes to each other.
Figure 9B:
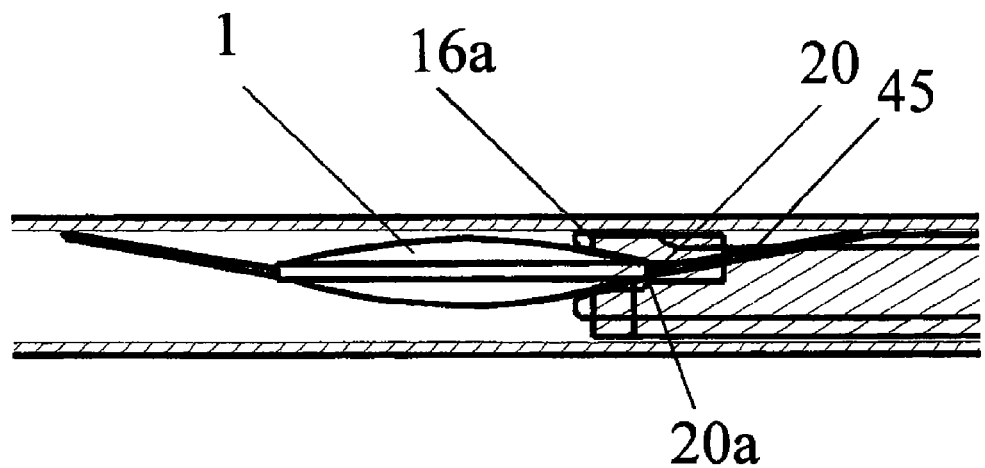
FIG. 9B is a side view showing a case where a front end of the lens holding member and the outline of the lens have similar shapes to each other.

For example, FIGS. 7, 9A and 9B show an example in which the lens 1 is held with an interlocking member 45 movable together with the pushing shaft 16 in the main body 12 (lens housing portion 12b). A bifurcated portion 20 that holds the lens 1 and an inclined surface 15 that keeps an angle of the rear side support portion 1b (angle at which the rear side support portion 1b extends obliquely upward from the optical portion 1a) are provided in the interlocking member (lens holding member) 45.

The bifurcated portion 20 holds so as to sandwich the optical portion 1c of the lens 1 between its upper and lower inner surfaces, and a vertical surface 20a which is formed as an inner surface of the bifurcated portion 20 and has an arcuate shape contacts an outer edge of the optical portion 1a of the lens 1, thereby preventing rearward displacement of the lens 1. As shown in FIG. 9A, the vertical surface 20a has an arcuate shape similar to an arcuate shape of the outer edge of the optical portion 1a of the lens 1 in top view, which enables to stably hold the lens 1. Further, as shown in FIG. 9B, if the upper and lower inner surfaces of the bifurcated portion 20 have a shape similar to upper and lower surfaces of the optical portion 1a in side view, the lens 1 can be more stably held.

Figure 10:
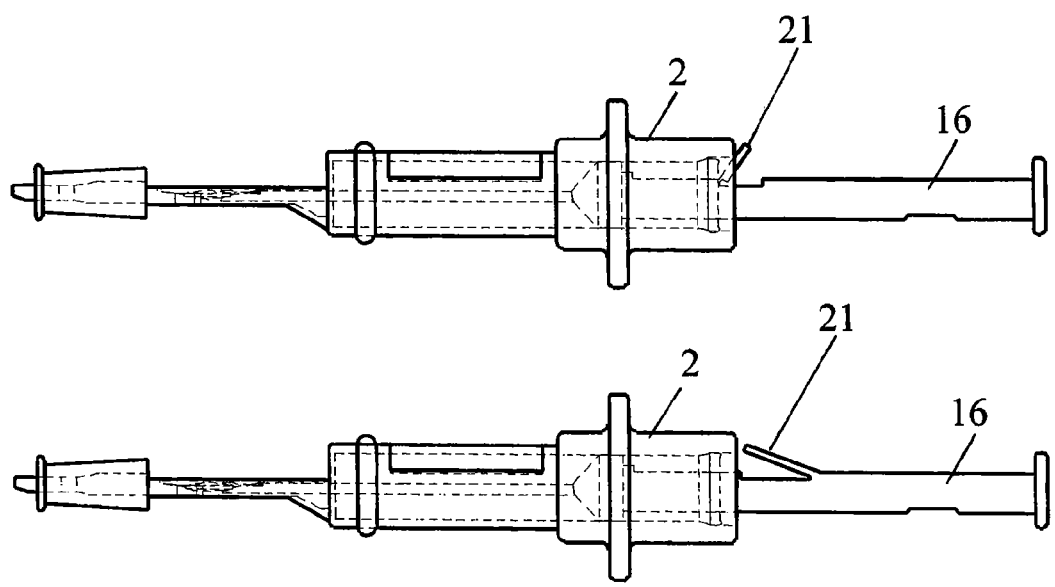
FIG. 10 shows a shape for preventing displacement of the pushing shaft.
Figure 11:
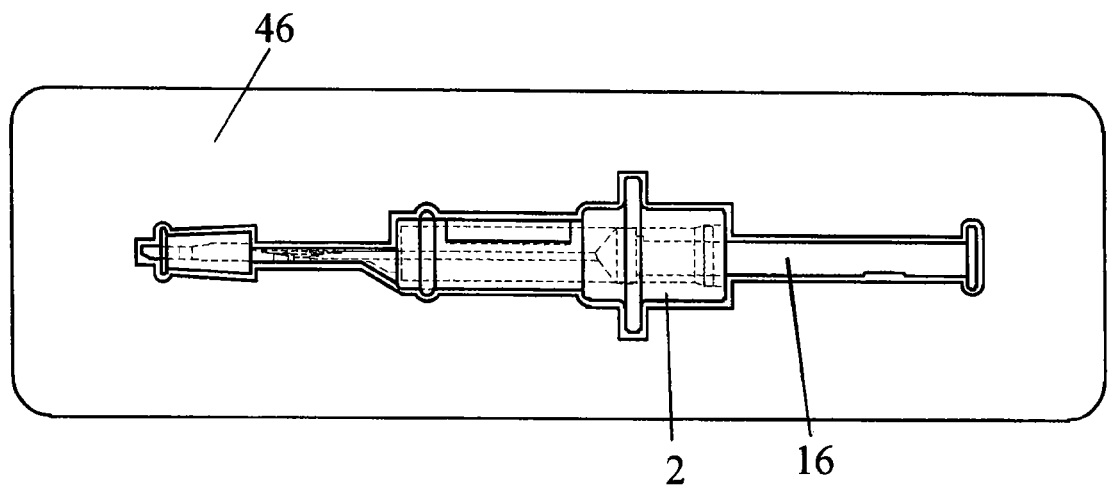
FIG. 11 shows the insertion device of the embodiment is placed in a carrier case.

In order to hold the lens 1 by the interlocking member 45 in the above-described initial state, it is necessary to prevent pushing of the pushing shaft 16 into the main body 12. Therefore, it is recommended that a locking portion 21 contacting the main body 12, as shown as two examples in FIG. 10, be formed on the pushing shaft 16, or resistance of the seal cap 44 attached on the pushing shaft 16 against the main body 12 be increased. Further, as shown in FIG. 11, from a factory shipment of the insertion device 2 up to just before surgery (also called as "in transportation"), the insertion device 2 in the initial state is contained in a case 46 and an inner surface shape of the case is made to correspond to a position and a shape of the pushing shaft 16 in the initial state, the pushing shaft 16 can be fixed with respect to the main body 12.

Figure 8:
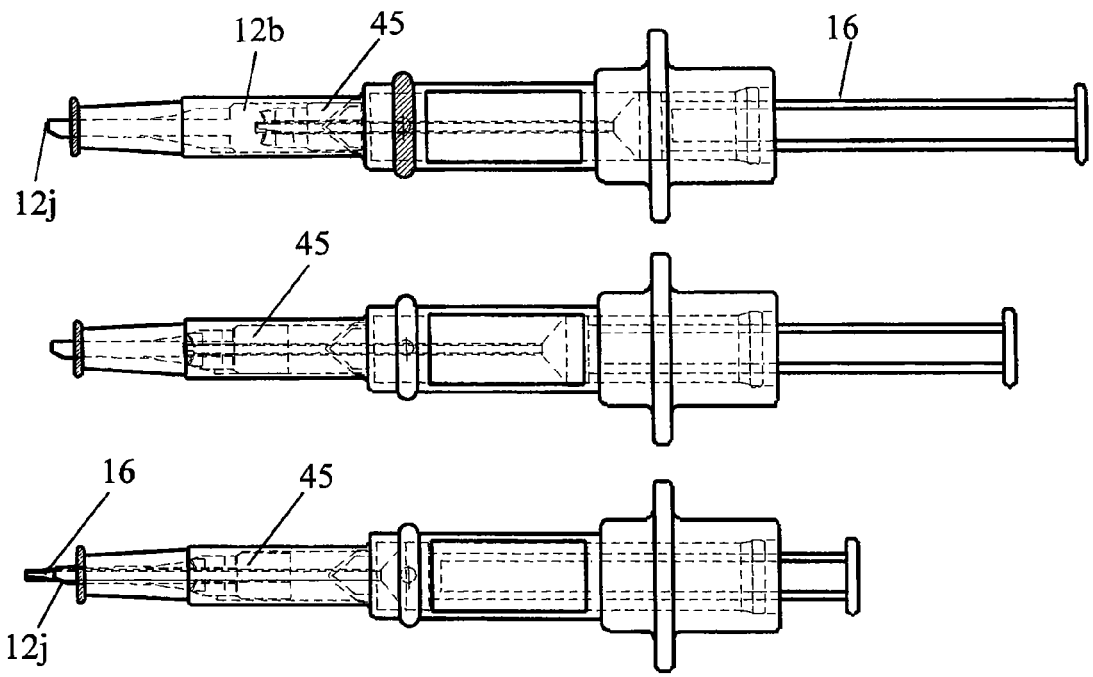
FIG. 8 is a view showing a situation of pushing out the lens in a case of using the interlocking member of FIG. 7.

As shown in FIG. 8, when the pushing shaft 16 is pushed into the main body 12 from the initial state (refer to the upper drawing) in which the pushing shaft 16 is not pushed into the main body 12, the interlocking member 45 and the lens 1 are moved together with the pushing shaft 16 in the lens housing portion 12b (refer to the middle drawing). Then, when a front end of the interlocking member 45 contacts a tapered portion 12p formed inside the lens housing portion 12b as shown in FIG. 7, further movement of the interlocking member 45 is prevented, and only the lens 1 is moved by the pushing shaft 16 toward the front end opening 12j while being folded in the nozzle portion 12c. In this way, the lens 1 is inserted into the eye. The lower drawing shows a state in which the lens 1 is inserted into the eye, and the front end of the pushing shaft 16 projects from the front end opening 12j.

The description was made of the case where only the interlocking member 45 is formed into the shape for preventing rearward displacement of the lens 1 and maintaining an angle of the supporting portion 1b. However, the pushing shaft 16 may also be formed into a shape having the same function.

Figure 12:
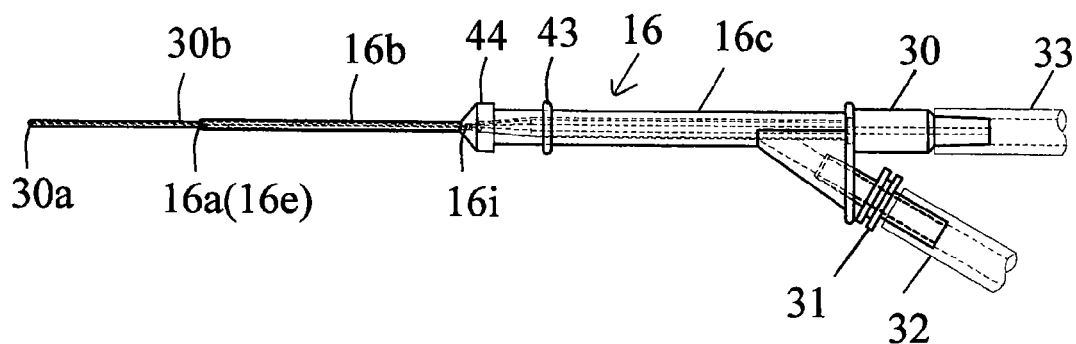
FIG. 12 shows the pushing shaft of the insertion device of the embodiment, the aspiration shaft and an ultrasonic phacoemulsification apparatus which are connected with each other using tubes.

FIG. 12 shows a state in which the aspiration shaft 30 described above and a connector 31 to which the perfusion tube 32 is connected are connected to the insertion device 2 of the embodiment.

Specifically, as described above, the thick shaft portion 30c and the thin shaft portion 30b of the aspiration shaft 30 are respectively inserted into the thick shaft hole 16g and the thin shaft hole 16f in the pushing shaft 16 through the rear end opening 16h thereof, and the thick shaft portion 30c of the aspiration shaft 30 is pressed into the rear end side portion (aspiration shaft connecting portion) of the thick shaft portion 16c (thick shaft hole 16g) of the pushing shaft 16. Insertion of the aspiration shaft 30 up to a position at which the O-ring 30d attached on the aspiration shaft 30 is brought into press-contact with the inner surface of the thick shaft hole 16g of the pushing shaft 16 causes the front end portion 30a of the thin shaft portion 30b of the aspiration shaft 30 to project from the front end opening 16e of the pushing shaft 16. In this way, the aspiration shaft 30 is connected to the pushing shaft 16, i.e., the insertion device 2.

Moreover, the connector 31 is pressed into the perfusion tube connecting hole 16j (conical hole portion 16k) of the perfusion tube connecting portion 16m formed in the pushing shaft 16. The perfusion tube 32 through which perfusate (liquid) from the ultrasonic phacoemulsification apparatus passes is connected to the connector 31.

Figure 13:
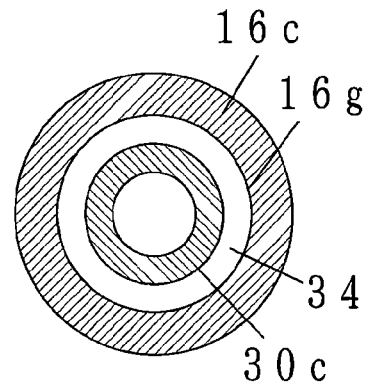
FIG. 13 is a sectional view of the pushing shaft of the insertion device of the embodiment and the aspiration shaft.

FIG. 13 shows a section of the thick shaft portion 16c in a state in which the aspiration shaft 30 is connected to the pushing shaft 16. A perfusion path 34 connected to the perfusion tube connecting hole 16j is formed between the inner circumferential surface of the thick shaft portion 16c (thick shaft hole 16g) and the outer circumferential surface of the thick shaft portion 30c. The perfusion path 34 is connected up to the intermediate hole 16i formed in the pushing shaft 16.

The description was made of the case where the perfusion path 34 is formed by inserting the aspiration shaft 30 into the pushing shaft 16. However, the space (thick shaft hole 16g) used as the perfusion path 34 is formed in advance of the insertion of the aspiration shaft 30 into the pushing shaft 16. It can be said from this standpoint that the insertion device 2 into which the aspiration shaft 30 is not inserted also has a perfusion path. Further, the inside of the thin shaft hole 16f in the pushing shaft 16 is almost occupied by the thin shaft portion 30b of the aspiration shaft 30.

In FIG. 13, the case has been described where the aspiration shaft 30 is placed coaxially with respect to the pushing shaft 16. However, the present invention is not limited to this case as long as a perfusion path is formed in a pushing shaft. For example, it is allowed that a thick shaft hole in a pushing shaft may be divided into two by a thick shaft portion of an aspiration shaft, and a perfusion path may be formed in one of the divided areas.

Figure 14:
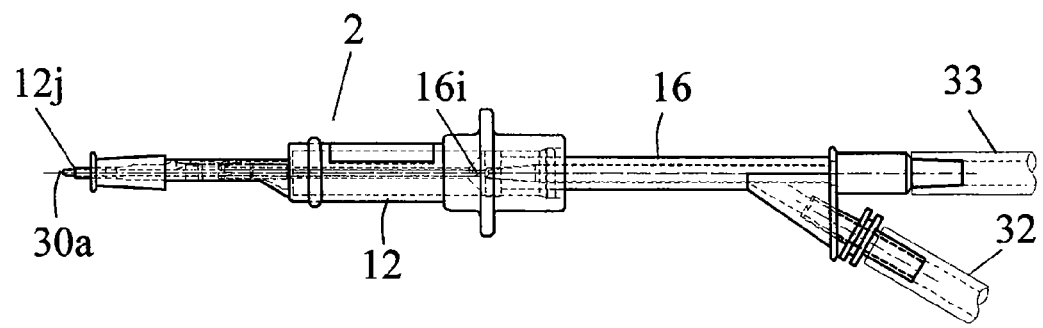
FIG. 14 shows the entire insertion device of the embodiment.

FIG. 14 shows a state in which the aspiration tube 33 and the perfusion tube 32 are connected to the insertion device 2. When the perfusate is made to flow into the perfusion path 34 in the insertion device 2 from the ultrasonic phacoemulsification apparatus (outside of the insertion device 2), the inside of the main body 12 is filled with the perfusate flowing out through the intermediate hole 16i (hole formed in the seal cap 44) of the pushing shaft 16. Thereafter, the perfusate flows out through the front end opening 12j of the nozzle portion 12c.

Figure 15:
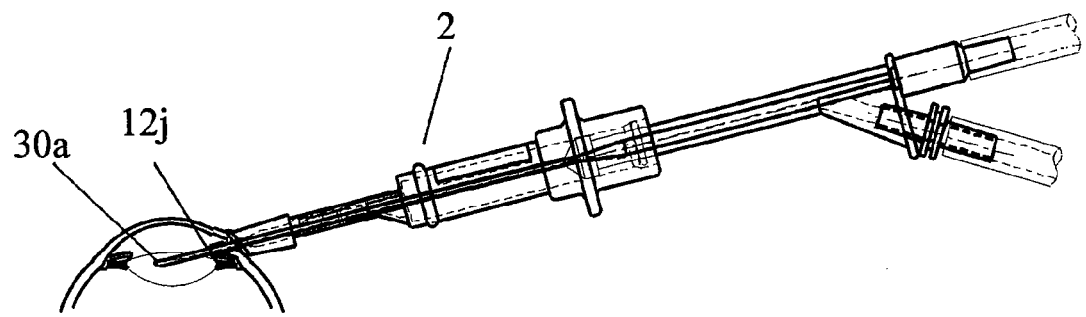
FIG. 15 shows an I/A process in a cataract surgery using the insertion device of the embodiment.

FIG. 15 shows a situation in which, in a cataract surgery, the nozzle portion 12j is inserted into the eyeball through an incision formed in the eyeball in a state in which the front end portion 30a of the aspiration shaft 30 projects from the front end opening 12j of the nozzle portion 12j after removing a clouded crystalline lens by a phacoemulsification tip. In this state, an I/A process for the cataract surgery is performed. That is, the perfusate existing in the eyeball together with the cortex which has not been removed by the phacoemulsification tip is aspirated by the ultrasonic phacoemulsification apparatus through the aspiration shaft 30 whose front end portion 30a projecting from the front end opening 12j of the nozzle portion 12j inserted into the eyeball, and the aspiration tube 33.

Meanwhile, the insertion device 2 of this embodiment is an intraocular lens preloaded insertion device (preloaded type insertion device) which is shipped in a state in which the lens 1 is loaded (installed) in the lens housing portion 12b from a factory, and is to be stored in a hospital until a surgery.

Figure 16A:
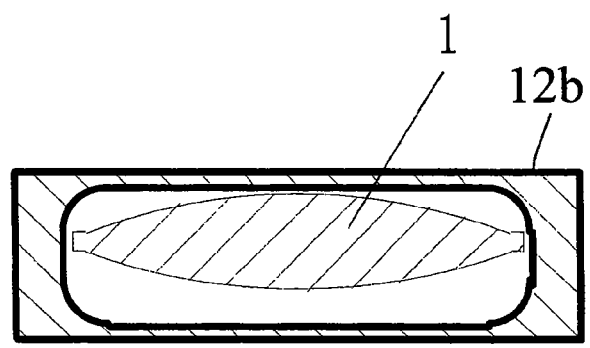
FIG. 16A is a sectional view showing a lens housing portion of the main body of the conventional insertion device.
Figure 16B:
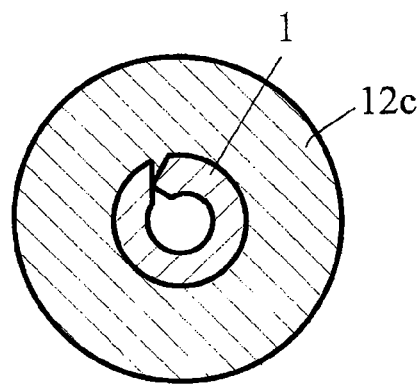
FIG. 16B is a sectional view showing the nozzle portion of the main body of the conventional insertion device.

In the preloaded type insertion device, the lens 1 in a state of being pushed by the pushing shaft 16 is not deformed as shown in FIG. 16A, and as the lens 1 is pushed into the nozzle portion 12c and moved thereinside by the pushing shaft 16, as shown in FIG. 16B, the lens 1 is folded to be deformed smaller.

Figure 17:
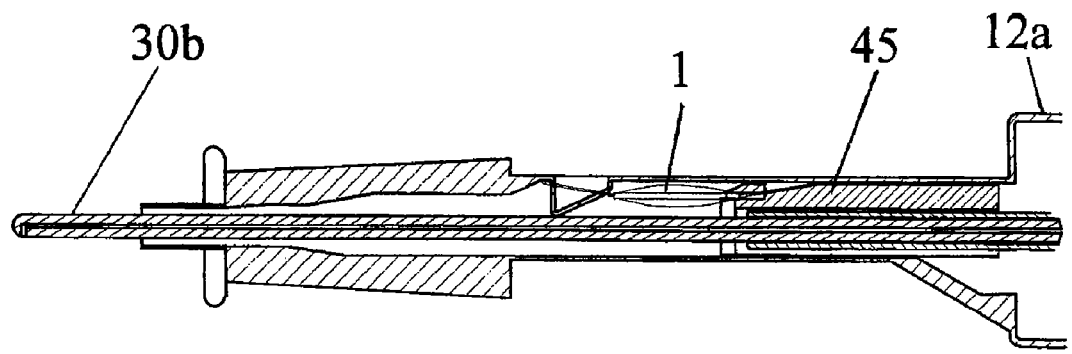
FIG. 17 is a sectional view showing a lens housing portion of the insertion device of the embodiment.

However, in this embodiment, since the aspiration shaft 30 is inserted into the inside of the pushing shaft 16, if the lens 1 is held coaxially with the pushing shaft 16, the lens 1 and the thin shaft portion 30b of the aspiration shaft 30 interfere with each other. Thus, in this embodiment, as shown in FIG. 17, the lens 1 before being pushed by the pushing shaft 16 is held by the interlocking member 45 at a position at which the lens 1 does not interfere with the thin shaft portion 30b of the aspiration shaft 30. The interlocking member 45 shown in FIG. 17 is located at a position, which is changed from that of the interlocking member 45 shown in FIGS. 8, 9A and 9B, where the lens 1 held by the interlocking member 45 is located at a higher position than that through which the thin shaft portion 30b of the aspiration shaft 30 passes.

Figure 18:
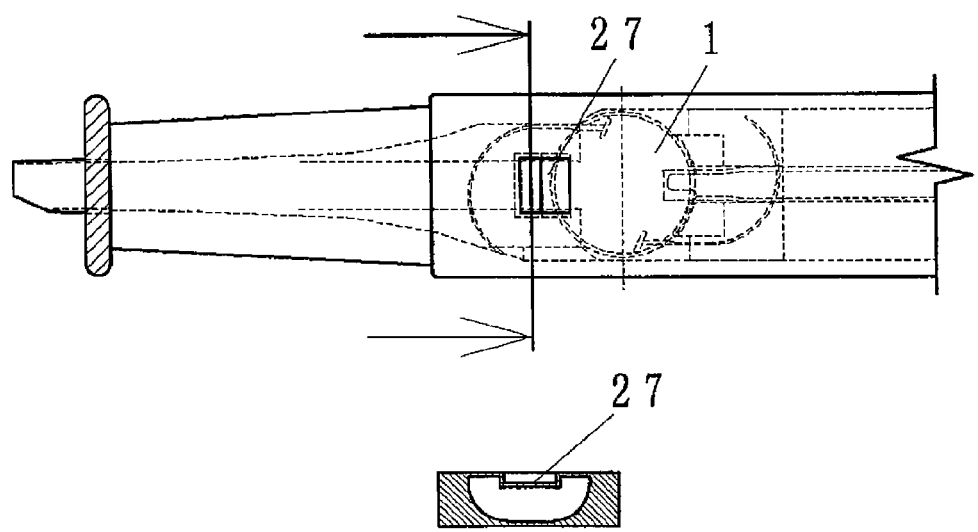
FIG. 18 is a sectional view of a lens guiding protrusion provided in the conventional insertion device.

Further, when using such an interlocking member 45, in order to move down the lens 1 to a position coaxial with the pushing shaft 16 after withdrawing the aspiration shaft 30 as will be described later, it is necessary to provide a protrusion 27 shown in FIG. 18 on a top surface at an intermediate position of the lens housing portion 12b in the axial direction. However, in the main body 12 in which the nozzle portion 12c is integrally formed and the rail 29 for guiding the lens 1 is formed in the inner side of the nozzle portion 12c, it is difficult in some cases to form the protrusion 27 which is relatively large from the standpoint of mold structure.

In other words, in a case where the inner surface of the main body 12 with the nozzle portion 12c is manufactured using one mold, it is necessary to slide the mold toward the rear end of the main body 12 at which the large rear end opening 12i is formed to remove the mold from the main body 12. Therefore, it is extremely difficult to form the protrusion 27 having a necessary size at the intermediate position of the lens housing portion 12b.

Thus, in this embodiment, after removing the mold that has formed the inner surface of the main body 12 with the nozzle portion 12c, at the intermediate position of the lens housing portion 12b in the axial direction, the top surface of the main body 12 is heated and deformed from the outside toward the inside to form the protrusion 27 having a size sufficient for deforming the lens 1 in a predetermined direction.

Figure 19:
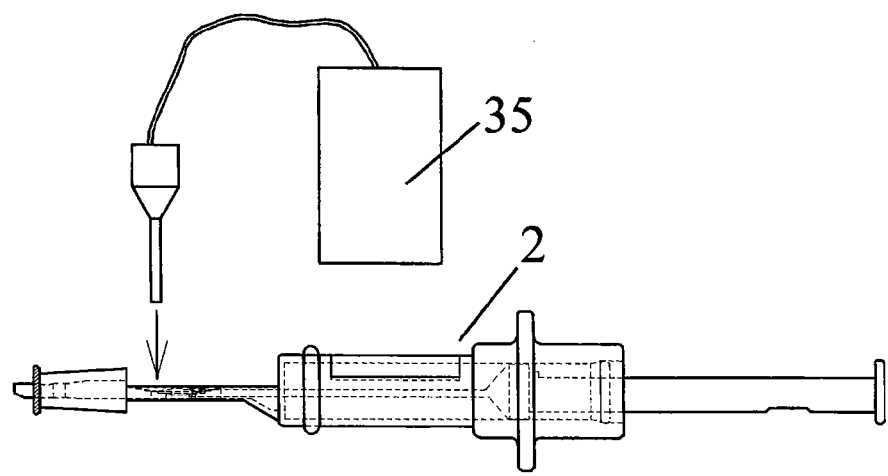
FIG. 19 is a view showing the lens housing portion deformed by heat.

Since sterile medical instruments are heated in some cases, it is preferable to form the protrusion 27 by the above-described method. In order to form the protrusion 27, as shown in FIG. 19, it is recommended to push a heating press device 35 onto the top surface of the main body 12. For example, in a case in which a thickness of the top surface of the main body 12 onto which the heating press device 35 is pressed is 0.5 mm, the heating press device 35 is heated to be approximately 120 degrees to be pressed onto the top surface of the main body 12 at constant pressure, which can form the protrusion 27 into a stable shape.

Figure 20:
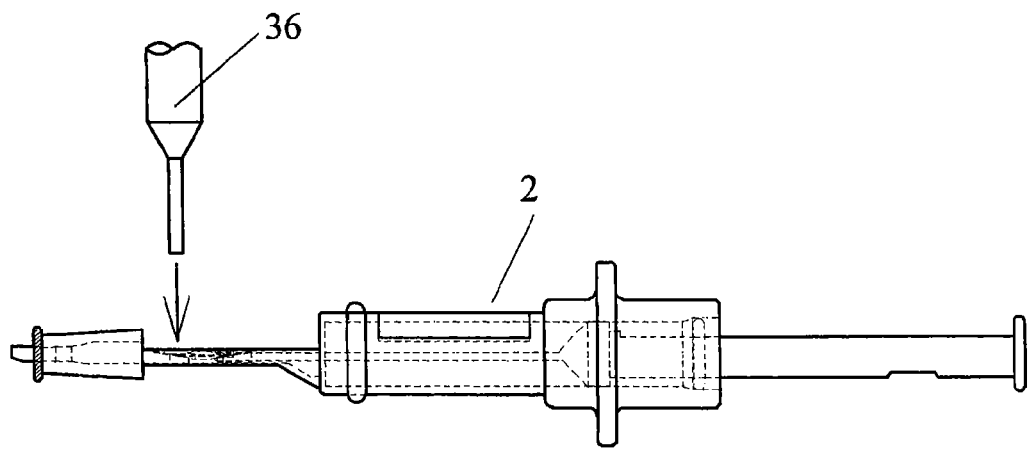
FIG. 20 is a view showing the lens housing portion deformed by a constant pressure.

Further, it is also allowed that the protrusion 27 may be formed, as shown in FIG. 20, by using a punch 36 to which constant pressure is applied.

Figure 21:
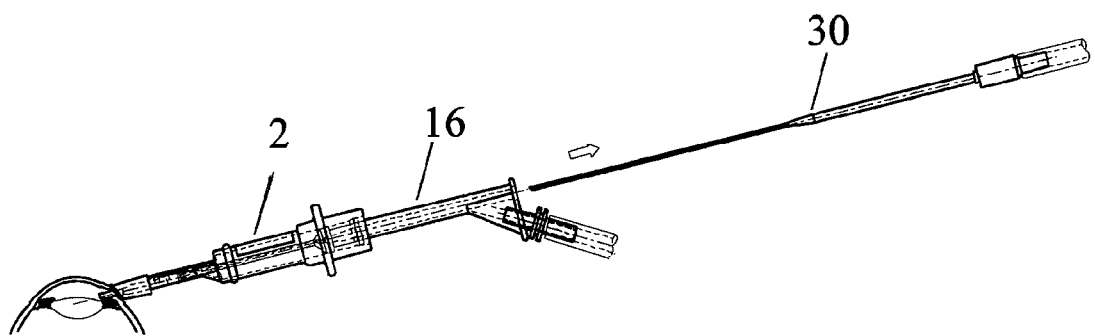
FIG. 21 shows the insertion device of the embodiment from which the aspiration shaft is detached after the I/A process.

After completion of the I/A process for the cataract surgery, as shown in FIG. 21, in the state where the nozzle portion 12c of the insertion device 2 is inserted in the eye, the aspiration shaft 30 is withdrawn from the insertion device 2 rearward to be detached therefrom.

Figure 22A:
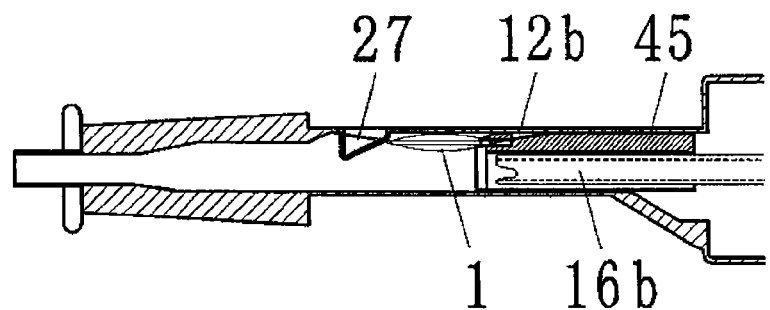
FIG. 22A shows a first state of the insertion device of the embodiment when pushing out the lens.
Figure 22B:
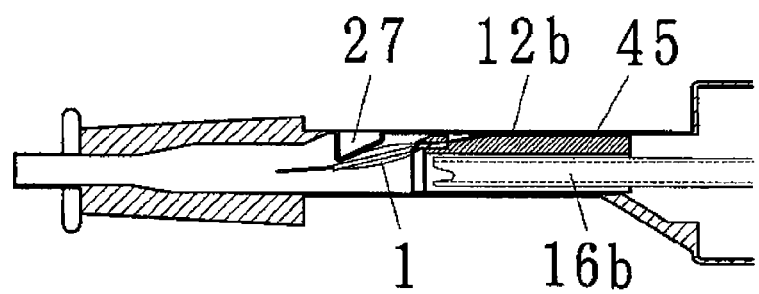
FIG. 22B shows a second state of the insertion device of the embodiment when pushing out the lens.
Figure 22C:
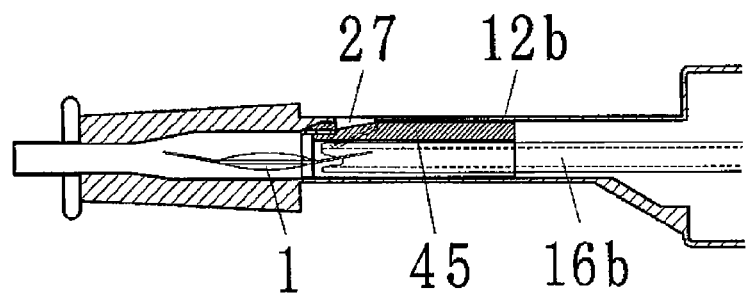
FIG. 22C shows a third state of the insertion device of the embodiment when pushing out the lens.

Thereafter, the pushing shaft 16 is pushed from the state shown in FIG. 22A (first state) to move the interlocking member 45 together with the lens 1 frontward. Thereby, as shown in FIG. 22B, the lens 1 is pushed down by the protrusion 27, and is deformed so as to be convex downward by a protrusion (not shown) formed on the top surface of the main body 12 (second state). Then, as shown in FIG. 22C, the lens 1 is placed at the position coaxial with the pushing shaft 16 at a timing when the interlocking member 45 comes into contact with the tapered portion 12p formed on the inner side of the main body 12 and thereby the interlock of the interlocking member 45 with the pushing shaft 16 is released (third state).

Figure 22D:
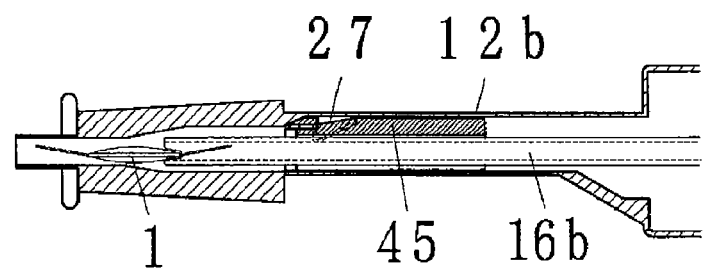
FIG. 22D shows a fourth state of the insertion device of the embodiment when pushing out the lens.
Figure 22E:
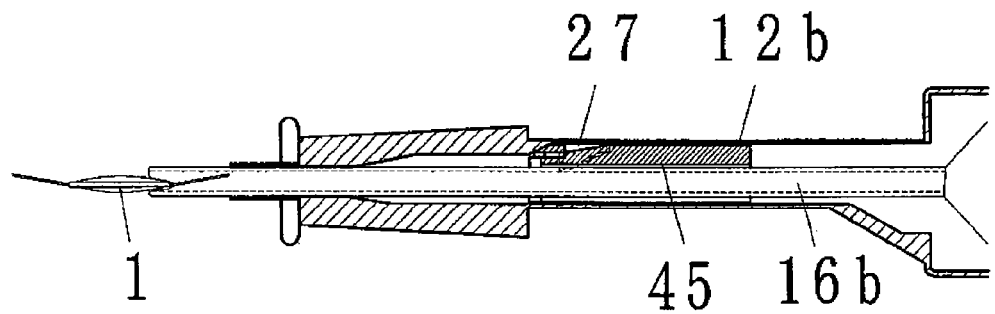
FIG. 22E shows a fifth state of the insertion device of the embodiment when pushing out the lens.
Figure 23:
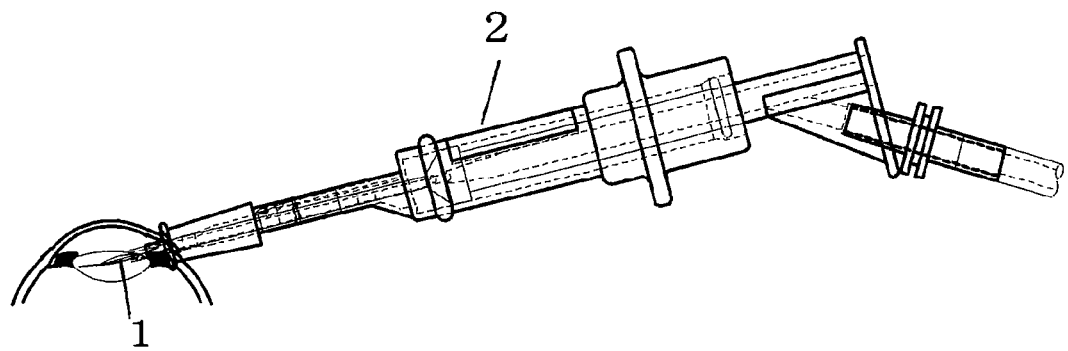
FIG. 23 shows that the lens is inserted into an eyeball from the insertion device of the embodiment.

Further pushing of the pushing shaft 16 from the third state folds, as shown in FIG. 22D, the lens 1 in the nozzle portion 12c (fourth state), and then, finally, as shown in FIG. 22E, the lens 1 is ejected through the front end opening 12j of the nozzle portion 12c (fifth state). FIG. 23 shows a situation in which the lens 1 is ejected into the eye.

After the aspiration shaft 30 is withdrawn from the insertion device 2 rearward to be detached therefrom, it is recommended to operate the pushing shaft 16 while covering the rear end opening 16h formed in the thick shaft portion 16c of the pushing shaft 16 with a finger or the like. Further, in the processes from the first state to the fifth state, an appropriate amount of perfusate adjusted by the ultrasonic phacoemulsification apparatus is introduced into the insertion device 2 through the rear end opening 16l of the perfusion tube connecting portion 16m of the pushing shaft 16.

Figure 24:
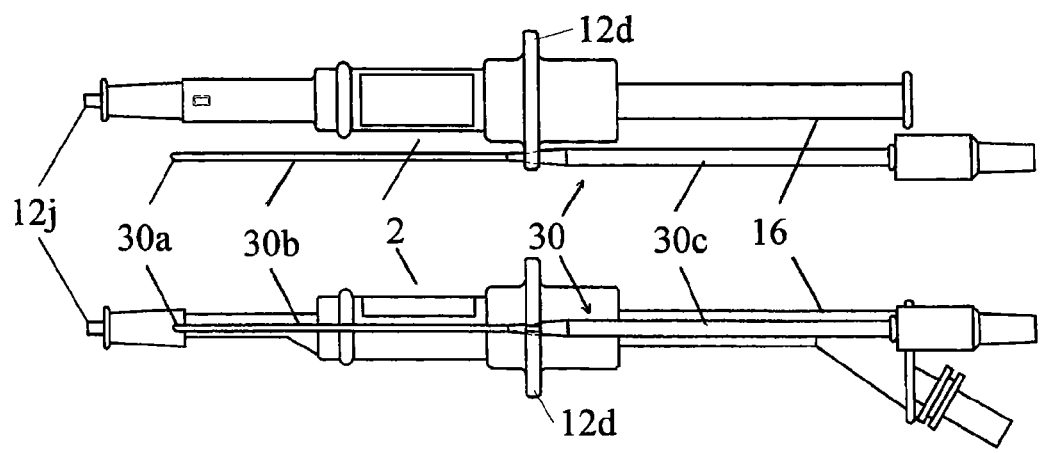
FIG. 24 is a top view and a side view showing a method for fixing the aspiration shaft drawn out from the main body in the insertion device of the embodiment.
Figure 25:
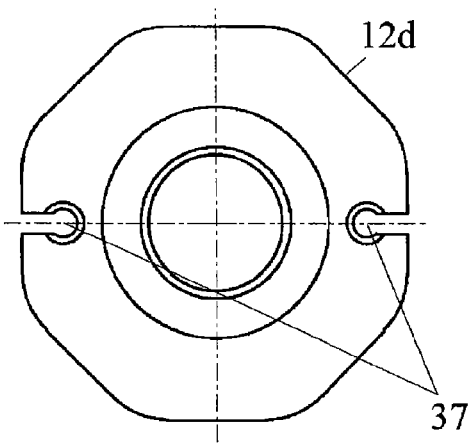
FIG. 25 is an external view showing a fixing portion for the aspiration shaft drawn out from the main body in the insertion device of the embodiment.
Figure 26:
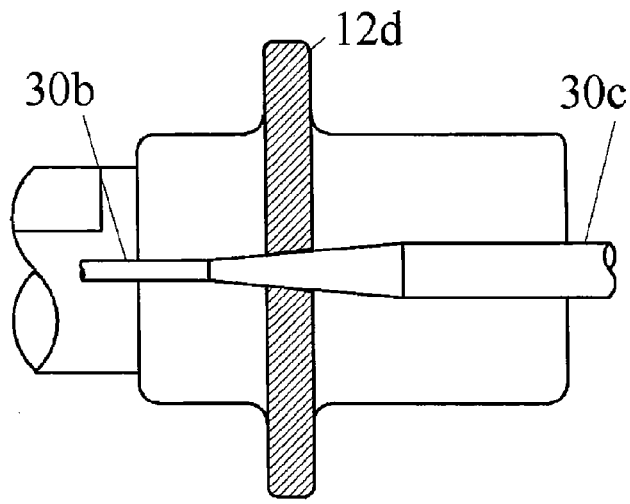
FIG. 26 is a sectional view showing the fixing portion.

It is recommended to fix the aspiration shaft 30 detached from the pushing shaft 16 to the insertion device 2 as shown in FIG. 24 in order not to interrupt the surgery. Specifically, as shown in FIG. 25, concave portions 37 are formed on both side surfaces of the flange portion 12d of the main body 12, and the aspiration shaft 30 is inserted into the concave portions 37 from the rear side or laterally. The concave portions 37 have its inner surface shape corresponding to a conical surface formed between the thin shaft portion 30b and the thick shaft portion 30c of the aspiration shaft 30 as shown in FIG. 26, in order for the front end portion 30a of the aspiration shaft 30 fixed to the insertion device 2 not to project from the front end opening 12j of the nozzle portion 12c.

Further, an aspiration shaft fixing side on which the aspiration shaft 30 is fixed to the insertion device 2 is preferably a side opposite to a dominant arm of an operator. Therefore, as shown in FIG. 25, the concave portions 37 are formed at the right and left of the flange portion 12d, which enables use of the both concave portions 37. Further, a male screw is formed on the conical surface formed between the thin shaft portion 30b and the thick shaft portion 30c of the aspiration shaft 30, and a female screw is formed on the inner surfaces of the concave portions 37, and engagement of these screws enables the aspiration shaft 30 to be more firmly fixed to the insertion device 2.

Figure 27:
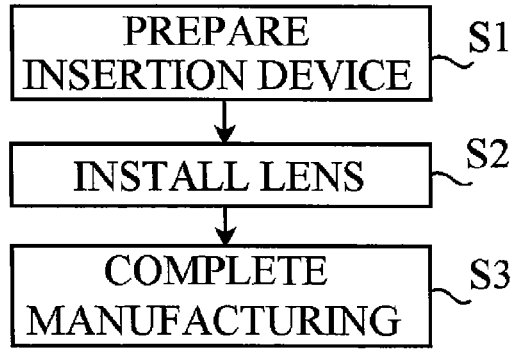
FIG. 27 is a flowchart showing a method for manufacturing an intraocular lens preinstalled insertion device.

FIG. 27 shows a method for manufacturing the preloaded type insertion device 2 of the embodiment. The insertion device 2 is manufactured through a step (step S1) of preparing the insertion device 2, in other words, the main body 12, the pushing shaft 16, the interlocking member 45 and the like before housing the lens 1 into the insertion device 2, and a step (step S2) of housing and holding, i.e., of installing the lens 1 in the lens housing portion 12c. In a case in which the aspiration shaft 30 also constitutes part of the insertion device, the aspiration shaft 30 is also prepared at step S1. In this case, at step S2, the aspiration shaft 30 may be fixed to the insertion device 2 as shown in FIG. 24. The insertion device 2 in which the lens 1 has been housed is sterilized and packaged, which completes the manufacturing process (step S3).

As described above, the insertion device 2 of this embodiment has the function of aspirating the cortex and the perfusate from the eye in the VA process and the function of inserting the lens 1 into the eye. This insertion device 2 can decrease the number of insertion and withdrawal of the insertion device 2 with respect to the incision formed on the eyeball from three to two, which enables reduction of a burden on the eyeball.

While the present invention has been described with reference to exemplary embodiments, it is to be understood that the invention is not limited to the disclosed exemplary embodiments. The scope of the following claims is to be accorded the broadest interpretation so as to encompass all such modifications, equivalent structures and functions.

We claim:

1. An insertion device for inserting an intraocular lens into an eye, comprising:
   a main body including a lens housing portion in which said intraocular lens is housed and a nozzle portion for ejecting the lens into the eye;
   a pushing shaft inserted into said lens housing portion and said nozzle portion of said main body, for moving the lens from said lens housing portion and pushing out the lens into the eye through a front end opening of said nozzle portion;
   a perfusion path formed by a space in said pushing shaft and communicated through a perfusion tube connecting hole with an outside of said insertion device, said perfusion path being communicated with said lens housing portion through an intermediate hole formed in said pushing shaft, for flowing liquid provided from the outside of said insertion device, into the eye through said lens housing portion and the front end opening of said nozzle portion; and
   an aspiration shaft capable of being inserted through a shaft hole of said pushing shaft to project a front end portion of said aspiration tube from a front end opening of said pushing shaft, said projected front end portion of said aspiration tube being capable of projecting into the eye from the front end opening of said nozzle portion, the aspiration shaft communicating said projected front end portion with an aspiration tube connected to a rear end of said aspiration shaft, for aspirating the liquid that was flowed into the eye,
   said perfusion path being formed between an inner circumferential surface of said shaft hole of said pushing shaft and an outer circumferential surface of said aspiration shaft when said aspiration shaft is inserted in said pushing shaft.

2. An intraocular lens preloaded insertion device comprising:
   the insertion device according to claim 1; and
   an intraocular lens held in the lens housing portion of the insertion device.

3. A method for manufacturing an intraocular lens preloaded insertion device comprising the steps of:
   preparing the insertion device according to claim 1; and causing the lens housing portion of the insertion device to hold the intraocular lens.

* * * * *

UNITED STATES PATENT AND TRADEMARK OFFICE
CERTIFICATE OF CORRECTION

PATENT NO.         : 8,454,625 B2                                    Page 1 of 1
APPLICATION NO.    : 12/629667
DATED              : June 4, 2013
INVENTOR(S)        : Katsumi Yoshida et al.

It is certified that error appears in the above-identified patent and that said Letters Patent is hereby corrected as shown below:

In the Specifications

Column 9, line 6, before "position" delete "180□" and insert instead --180°--.

Column 10, line 25, after "enables" insert --it--.

Signed and Sealed this
Twenty-fifth Day of February, 2014

Michelle K. Lee
*Deputy Director of the United States Patent and Trademark Office*